United States Patent [19]
Hoskin et al.

[11] Patent Number: 5,810,881
[45] Date of Patent: *Sep. 22, 1998

[54] CLAMPING OR GRIPPING DEVICES AND METHOD FOR PRODUCING THE SAME

[75] Inventors: William John Hoskin, deceased, late of Harpenden, by Elizabeth Anne Newell legal representative; Nicholas Richard Kemp, Luton, both of United Kingdom

[73] Assignee: Microsurgical Equipment Ltd., Luton, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 635,929

[22] PCT Filed: Oct. 13, 1994

[86] PCT No.: PCT/GB94/02242

§ 371 Date: Apr. 25, 1996

§ 102(e) Date: Apr. 25, 1996

[87] PCT Pub. No.: WO95/11629

PCT Pub. Date: May 10, 1995

[30] Foreign Application Priority Data

Oct. 28, 1993 [GB] United Kingdom .................. 9322240

[51] Int. Cl.⁶ ..................................................... A61B 17/28
[52] U.S. Cl. .......................... 606/207; 606/147; 606/148; 81/421; 81/426.5; 269/275
[58] Field of Search ..................................... 606/148, 207, 606/147, 210; 600/564; 433/159; 81/418, 421, 426.5; 269/257, 271, 273, 275

[56] References Cited

U.S. PATENT DOCUMENTS

| 2,706,987 | 4/1955 | Bramstedt | 606/147 |
| 5,242,458 | 9/1993 | Bendel et al. | 606/147 |
| 5,509,923 | 4/1996 | Middleman et al. | 606/207 |

FOREIGN PATENT DOCUMENTS

| 416689 | 1/1924 | Germany . |
| 086792 | 5/1982 | United Kingdom . |

*Primary Examiner*—Michael H. Thaler
*Attorney, Agent, or Firm*—Christie, Parker & Hale, LLP

[57] ABSTRACT

A surgical needle holder has the facing surfaces of its jaws lined with memory alloy which is soft enough to distort around a needle when gripped between the jaws. A better grip on the needle is thus achieved. The surfaces of the inserts may be profiled with ribs to allow the alloy to be subject to a greater pressure per square centimeter locally and so more readily deformed.

14 Claims, 1 Drawing Sheet

ND METHOD FOR PRODUCING THE SAME

CLAMPING OR GRIPPING DEVICES AND METHOD FOR PRODUCING THE SAME

BACKGROUND OF THE INVENTION

The present invention relates to clamping or gripping devices, for example, surgical needle holders.

Surgical needle holders include a pair of articulated jaws which are brought together to clamp or grip a surgical needle. Such needle holders are often required to hold needles having different sizes and shapes and because the area of contact between the surface of the needle (which is usually circular), and the surface of the jaws (which is usually planar) is relatively small, the needle is liable to shift relative to the jaws during a stitching operation.

SUMMARY OF THE INVENTION

It is an object of the invention to provide an improved clamping or gripping device.

According to the present invention there is provided a clamping or gripping device comprising a pair of cooperating jaws, at least one of the two facing surfaces of the jaws comprising a memory material which is deformed by an object when gripped between the two jaws, to increase the grip by the jaws on the object, the memory material being capable of resuming its original shape when released from the object by being subjected to a temperature in excess of a predetermined temperature.

According to the present invention there is further provided a method of producing a clamping or gripping device comprising the steps of providing a pair of articulated jaws, lining the surface of at least one of the two facing surfaces of the jaws with an insert of memory material and profiling the surface of the insert to have an undulating pattern when in its heat stable state.

Surgical needle holders embodying the present invention will now be described, by way of example, with reference to the accompanying drawings.

DETAILED DESCRIPTION

Figure 1:
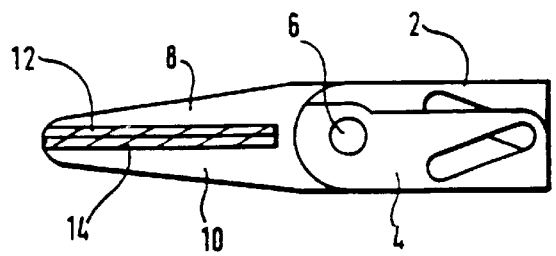
FIG. 1 is a fragmentary side elevation of the needle holder.
Figure 2:
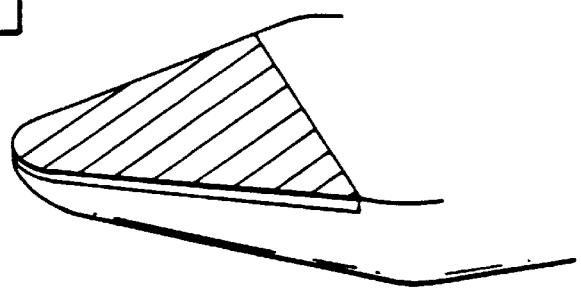
FIG. 2 is a fragmentary perspective view of one of the jaws of the needle holder.

The needle holder shown in FIG. 1 comprises a pair of arms 2 and 4 pivotally secured together by a pin 6. Each arm 2 and 4 carries a respective jaw 8 and 10. The facing surfaces of the jaws 8 and 10 are provided with a respective metallic insert 12 and 14.

In operation, a needle carrying a suture is placed between the inserts 12 and 14 of the jaws and the jaws 8 and 10 are brought together by operating the arms 2 and 4 to clamp the needle between the inserts 12 and 14. The needle can have a variety of shapes, it can be curved, straight or otherwise profiled.

Each insert, which is advantageously 1 mm thick, is fitted in a recess of a respective jaw and is bonded thereto by brazing, soldering, gluing, mechanical clamping, riveting or sintering.

Each insert is of memory material, for example, a metal or alloy.

Materials which possess shape memory are known. Articles made of such materials can be deformed from a first undeformed configuration to a second deformed configuration. Such articles revert to the undeformed configuration when subjected to specified conditions. They are said to have shape memory. One set of conditions which will enable a deformed configuration of an article having shape memory to recover toward its undeformed configuration or shape is the application of heat. The material thus has a first heat-stable configuration and a second, heat-unstable configuration. A selected alloy is formed into its heat-unstable configuration at a temperature at which it is in a predominantly martensitic phase. Upon application of heat, the alloy reverts or attempts to recover from its heat-unstable configuration towards its first heat-stable configuration, ie, it "remembers" its original shape.

The ability in metallic alloys to possess shape memory is because the alloy can undergo a reversible transformation from a predominantly austenitic state to a predominantly martensitic state with a decrease in temperature. This transformation is sometimes referred to as a thermoelastic martensitic transformation. An article made from such an alloy is easily deformed from its original configuration to a new configuration when cooled below the temperature at which the alloy is transformed from a predominantly austenitic state to a predominantly martensitic state.

The preferred metal alloy for the inserts 12 and 14 is a titanium nickel alloy containing 50% nickel and 50% titanium. Other memory metal alloys which are biologically acceptable can also be used.

The alloy used is sufficiently soft that when the inserts are clamped onto a needle, the inserts will partially deform around the needle and so hold the needle more firmly between the jaws. After several clamping actions, the surface of the inserts becomes badly deformed and distorted and in certain parts will deform no further. When this happens, the needle holders are placed in a heat sterilizer (at, for example, 110° C.) to raise the temperature of the alloy from a level at which it lies in its heat unstable configuration to a level at which it can resume its heat-stable configuration i.e. the inserts resume their previous undeformed shape. The needle holder is now both sterilized and reshaped ready to be used again.

In order to achieve a deformation of the surface of the insert with minimum force and effort and to achieve a satisfactory clamping action on the needle, the inserts may be specially profiled when in their undeformed state.

Figure 3:
FIG. 3 is a section through the jaws of a second embodiment of a needle holder.
Figure 3:
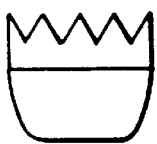

As shown in the embodiment of FIG. 3, the facing inserts 12 and 14 have mating teeth and cavities so that when the jaws are closed the tooth on one insert engages a corresponding cavity on the other insert and vice versa.

Figure 4:
FIG. 4 is a section through the jaws of a third embodiment of a needle holder.
Figure 4:
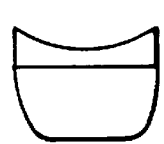

In the embodiment shown in FIG. 4, one insert has a concave surface profile while the other insert has a concave profile.

Figure 5:
FIG. 5 is a section through the jaws of a forth embodiment of a needle holder.

In the embodiment shown in FIG. 5, one insert has a central longitudinally extending rib while the other insert has two spaced lateral longitudinally extending ribs straddling the control rib.

Figure 6:
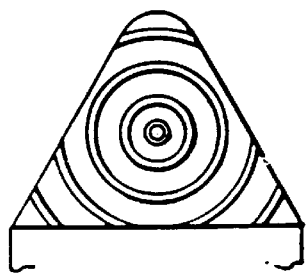
FIG. 6 is a plan view of one of the jaws of a fifth embodiment of the needle holder.
Figure 7:
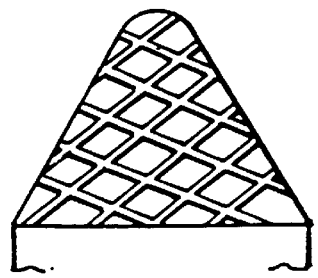
FIG. 7 is a plan view of one of the jaws of a fifth embodiment of a needle holder.

In the embodiment of FIG. 6, each insert is provided with concentric circular ribs while in FIG. 7 there are two sets of parallel ribs with one set intersecting the other set. The ribs may be in an array which emulates finger prints.

By using a series of ribs or teeth they are readily deformed by the needle which traverses them when the jaws are clamped together. The reduced area of the ribs enables them to be subjected to a greater pressure per square centimeter. The needle is thus imprisoned between the jaws and relative movement between the needle and the jaws is resisted.

The different profiles in the surface of the inserts can be achieved by casting or sintering the inserts in a profiled mold or by machining. If machining is employed, the profiles can either be directly machined into the surface or produced by an indirect method. The indirect method involves using a die having a negative image of the ribs and deforming the insert in its heat unstable state with the die. The insert resulting negative profile is machined flat and the insert is thereafter heated to a temperature at which it can adopt its heat stable configuration. As a result, a positive version of the negative die profile materializes.

With needle holders, it is important that the memory alloy used has a transition temperature in excess of the temperature of the human body but less than the temperature used for sterilization. A preferred range for the transition temperature is thus 60° C. to 120° C.

Memory alloy inserts are particularly useful in needle-holders used for laproscopic surgery.

It will be appreciated that the memory alloy inserts can be used in clamping and gripping devices other than needle holders.

It is claimed:

1. A clamping or gripping device comprising a pair of cooperating jaws having opposing surfaces, at least one of the opposing surfaces comprising a memory material having an original shape and being deformable by an object when the object is gripped between the two surfaces, the memory material comprising a material having a martensitic state when at body temperature and an austenitic state when heated to a predetermined temperature above body temperature, whereby the material will only resume said original shape following release from the object when subjected to a temperature in excess of said predetermined temperature.

2. A device according to claim 1 wherein each of the jaws has an insert of said memory material to define the opposing surfaces of the jaws.

3. A device according to claim 2 wherein each of the inserts has a thickness in the range of 0.5 to 2 mm.

4. A device according to claim 2 or to claim 3, wherein at least one of the inserts has an undulating surface profile to localize pressure applied by the jaws on the object and to achieve local deformation of the inserts.

5. A device according to claim 4 wherein each of the inserts has a surface profile comprising an array of mating teeth and cavities.

6. A device according to claim 4 wherein the surface profile comprises an array of parallel ribs.

7. A device according to claim 4 wherein each of the inserts has a surface profile comprising two arrays of parallel ribs, the ribs of one of the arrays intersecting the ribs of the other array.

8. A device according to claim 4 wherein the surface profile comprises an array of ribs arranged in concentric circles.

9. A device according to claim 4 wherein the surface profile comprises an array of ribs in a fingerprint-like pattern.

10. A device according to claim 1 wherein said memory material comprises a titanium nickel alloy.

11. A device according to claim 1 wherein said predetermined temperature is approximately 110° C.

12. A method for producing a clamping or gripping device comprising the steps of providing a pair of articulated jaws having opposing surfaces, lining at least one of the opposing surfaces of the jaws with an insert of memory material, said memory material having a martensitic state when at body temperature and an austenitic state when heated to a temperature above body temperature and profiling the insert to have an undulating pattern when in its austenitic state.

13. A method according to claim 12 wherein the step of profiling comprises machining a surface of the insert in its austenitic state.

14. A method according to claim 12 wherein the step of profiling comprises stamping a negative of said undulating pattern into the insert when in a martensitic state, machining the insert to provide a planar surface, and heating the memory material above body temperature to achieve its austenitic state and thereby cause a positive of said undulating pattern on the insert.

* * * * *